United States Patent [19]

Kerst

[11] 3,957,858

[45] May 18, 1976

[54] SUBSTITUTED ETHANE DIPHOSPHONIC ACIDS AND SALTS AND ESTERS THEREOF

[75] Inventor: Al F. Kerst, Littleton, Colo.

[73] Assignee: Monsanto Company, St. Louis, Mo.

[22] Filed: Aug. 23, 1972

[21] Appl. No.: 283,146

Related U.S. Application Data

[62] Division of Ser. No. 27,988, April 13, 1970, Pat. No. 3,705,191.

[52] U.S. Cl. .......................... 260/502.4 P; 210/58; 252/8.1; 252/8.6; 252/8.7; 252/8.8; 260/348 R; 260/348 A; 260/429 R; 260/429 J; 260/429.1; 260/429.2; 260/429.7; 260/431; 260/432; 260/435 P; 260/438.5 R; 260/439 R; 260/465.6; 260/501.1; 260/501.12; 260/501.19; 260/501.21; 260/502.5; 260/926; 260/932; 260/938

[51] Int. Cl.² .......................... C07F 9/39; C07F 9/29

[58] Field of Search ............. 260/502.4 P, 502.4 A, 260/501.21

[56] References Cited

UNITED STATES PATENTS

| | | | |
|---|---|---|---|
| 2,900,408 | 8/1959 | Blaser et al. | 260/502.4 A |
| 3,198,826 | 8/1965 | Calhoun | 260/502.4 R |
| 3,214,454 | 10/1965 | Blaser et al. | 260/502.4 A |
| 3,285,954 | 11/1966 | Uhing et al. | 260/502.4 R |
| 3,366,677 | 1/1968 | Quimby | 260/502.4 A |
| 3,475,486 | 10/1969 | Irani et al. | 260/502.4 A |
| 3,670,015 | 6/1972 | Prentice | 260/502.4 P |

FOREIGN PATENTS OR APPLICATIONS

1,010,965  6/1957  Germany .................... 260/502.4 A

*Primary Examiner*—Joseph E. Evans
*Attorney, Agent, or Firm*—Wayne R. Eberhardt

[57] ABSTRACT

New and useful substituted ethane diphosphonic acids and salts thereof as exemplified by the acid compound having the formula

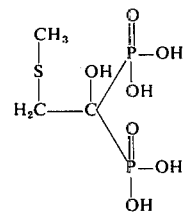

2-thiomethyl-1-hydroxy-ethane-1,1-diphosphonic acid and processes for preparing the same which generically comprise the "de-oxiranization" of an epoxy ethane diphosphonate having the formula

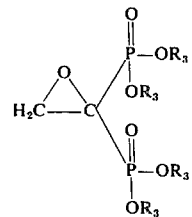

wherein $R_3$ is hydrogen, a metal ion, or an organic radical.

8 Claims, No Drawings

SUBSTITUTED ETHANE DIPHOSPHONIC ACIDS AND SALTS AND ESTERS THEREOF

This is a division, of application Ser. No. 27,988, filed Apr. 13, 1970 now U.S. Pat. No. 705,191

The present invention relates to a new class of ethane diphosphonate compounds and processes for preparing such compounds. More particularly, the present invention has as its primary object providing ethane diphosphonic acids as well as the salts and esters thereof, and processes for preparing the same.

According to the present invention, there is provided a new and useful class of ethane diphosphonate compounds corresponding to the following formula:

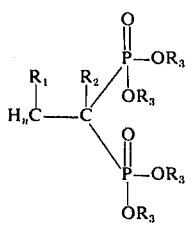
(I)

In the above formula I, $R_1$ can be from the group oxygen; halogen; hydroxy; —CN; —N($R_4$)$_2$, where $R_4$ is from the group hydrogen and alkyl containing from 1 to 30 carbon atoms, preferably from 1 to 8 carbon atoms and more preferably from 1 to 4 carbon atoms; —X$R_5$, where X is from the group oxygen and sulfur and $R_5$ is from the group alkyl containing from 1 to 30 carbon atoms, preferably 1 to 8 carbon atoms, more preferably 1 to 4 carbon atoms; $C_6H_5$ (phenyl) and $CH_2.C_6H_5$ (benzyl); acetoxy; —$SO_3R_4$ where $R_4$ is the same as defined above; benzoyl; —$CO_2H$; and —CH(COOR$_6$)$_2$, where $R_6$ is an alkyl group containing from 1 to 30 carbon atoms, preferably from 1 to 8 carbon atoms, and more preferably from 1 to 4 carbon atoms.

In the aforegoing general formula I, $R_2$ is from the group $R_1$, except oxygen, and hydrogen. It is to be understood that $R_2$ then is never oxygen and $R_2$ is only hydrogen when $R_1$ is oxygen. Additionally, it is to be understood that in all cases, except when $R_1$ is oxygen and $R_2$ is hydrogen, at least $R_1$ or $R_2$ is a hydroxy group. In other words and for exemplary purposes only, when $R_1$ is chlorine, $R_2$ must be a hydroxy group.

In conjunction with the proviso that $R_2$ is only hydrogen when $R_1$ is oxygen with reference to the aforegoing general formula I, $n$ is an integer having a value of 1 or 2 and $n$ is only 1 when $R_1$ is oxygen.

In formula I, $R_3$ individually is from the group metal ions, hydrogen, alkyl, alkenyl, aryl, alkyl, cyclic and alicyclic. The aforementioned metal ions are from the group of metals which includes without limitation alkali metals such as sodium, lithium and potassium; alkaline earth metals, such as calcium and magnesium; aluminum; zinc; cadmium; manganese; nickel; cobalt; cerium; lead; tin; iron; chromium; and mercury. Also included are ammonium ions and alkyl ammonium ions. In particular, those alkyl ammonium ions derived from amines having a low molecular weight, such as below about 300, and more particularly the alkyl amines, alkylene amines, and alkanol amines containing not more than two amine groups, the lower alkyl amines, e.g. ethyl amine, diethyl amine, propyl amine, [propylene diamine] hexy amine, 2-ethylhexylaninei propylene diamine N-butylethanol amine, triethanol amine, and the like, are the preferred amines. It is to be understood that the preferred metal ions are those which render the compound a water-soluble salt.

In conjunction with the foregoing general formula I and more specifically when the ethane diphosphonate is in the ester form thereof, i.e., $R_3$ is an organic radical heretofore mentioned, the preferred substituents are the following:

a. alkyl — containing from about 1 to about 18 carbon atoms;
b. alkenyl — containing from about 1 to about 18 carbon atoms;
c. aryl — phenyl, naphthyl, anthryl, or phenanthryl;
d. alkyl aryl — hydroxy, halogen, lower alkyl, (alkaryl) having from 1 to about 6 carbon atoms, and amino substituted phenyl, naphthyl, anthryl, or phenanthryl;
e. cyclic — containing from about 4 to about 8 carbon atoms and there may be present in the ring either a nitrogen, sulfur, oxygen or phosphorus atom; and
f. alicyclic — containing from about 4 to about 10 carbon atoms.

It is to be understood that all of the compounds falling within the above formula I and as heretofore defined are generically described herein as "ethane diphosphonates". In other words then, the acids, salts and esters and mixtures thereof are all generically described herein as ethane diphosphonates.

In genral, the ethane diphosphonates are prepared by contacting an epoxy ethane diphosphonate having the following formula:

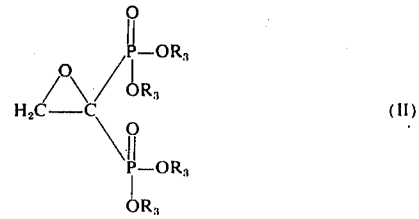
(II)

wherein $R_3$ is the same as defined above, with a de-oxiranization agent which opens the ring of said epoxy compound to form the ethane diphosphonates falling within formula I. It is to be understood that the term "epoxy ethane diphosphonate" used herein generically describes and encompasses the acid, salt and ester forms, and said term is designated at times herein EEDP for the sake of brevity.

The de-oxiranization agents which effect this "ring opening" are from the group ammonia, primary amines, secondary amines, acids, malonates, alcohols, mercaptans, Lewis acid catalysts and mixtures thereof. The specific application of these de-oxiranization agents are disclosed in the processes which are described hereinafter.

The aforementioned epoxy ethane diphosphonates which are one of the basic starting materials in conjunction with the preparation of the ethane diphosphonates falling within formula I are disclosed and described, as well as methods for preparing the same, in a co-pending application, entitled "Substituted Epoxy Ethane Polyphosphonic Acids, Esters and Salts Thereof", of Al Fred Kerst which is filed concurrently with the present application and which is incorporated herein by reference. For exemplary purposes only, this starting material, i.e., the epoxy ethane diphosphonate, utilized to prepare the ethane diphosphonates of the present invention, can be prepared by reacting the disodium salt of ethylene diphosphonic acid, i.e.,

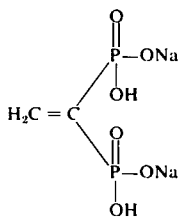

with hydrogen peroxide in the presence of a catalyst such as sodium tungstate. The above ethylene diphosphonate, also sometimes referred to in the art as vinylidene diphosphonate, known in the art (in its ester form and processes for preparing the same) as exemplified by U.S. Pat. No. 3,062,792, which is incorporated herein by reference. The aforementioned disodium salt can be obtained from the ester (U.S. Pat. No. 3,062,792) by mineral acid hydrolysis followed by reaction with sodium hydroxide. The ethylene diphosphonic acids and salts per se and processes for preparing the same are described in Canadian patent No. 811,736, which is incorporated herein by reference.

The following subject matter specifically illustrates the preparation of the ethane diphosphonates from EEDP.

HYDROLYSIS OF EPOXY ETHANE DIPHOSPHONATE

The hydrolyis of epoxy ethane diphosphonate to produce the dihydroxy ethane diphosphonate proceeds according to the following general reaction;

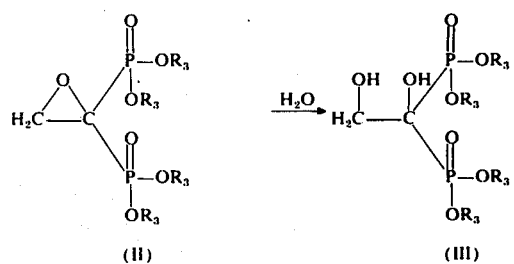

wherein $R_3$ is the same as defined above. The aforementioned reaction may be carried out by mixing the epoxy ethane diphosphonate in a sufficient volume of water, i.e., at least stoichiometric quantities, preferably a molar ratio of water to EEDP of 1:1 to 20:1, and heating the resultant mass until substantially complete hydrolysis occurs. The use of greater than stoichiometric quantities of water functions as a diluent for the reaction system. It is also found that substantially water-miscible organic diluents which have a boiling point between about 50°C and 150°C, preferably from about 70°C to about 100°C, such as dioxane, acetone, lower alcohols (e.g., methanol, ethanol, propanol and butanol) are suitable as a reaction medium or diluent in which the above-described hydrolysis reaction can be conducted.

The hydrolysis reaction may be accelerated by the addition of an acid catalyst (e.g., from 0.01 to 10% by weight based on the total weight of EEDP) such as $HClO_4$, $H_2SO_4$, HCl, benzene sulfonic acid, and the like. However, the use of an acid catalyst is not necessary in order to carry out the aforementioned reaction when $R_3$ of the EEDP is hydrogen in all cases or at least where 3 hydrogen atoms are present, but is desirable where EEDP is in the salt, partial salt, ester or partial ester form. Generally, the heating of the epoxy ethane diphosphonate in water takes place at a temperature above about 50°C, preferably from about 80°C to about 150°C, either under atmospheric, sub-atmospheric (e.g., ½ to 760 mm Hg), or super atmospheric (e.g., 1 to 10 atmospheres) conditions, and for a sufficient period of time, for example, from about five minutes to about two hours or more, depending upon the particular epoxy ethane dipshosphonate utilized as a starting material, and also if an acid catalyst is utilized, to facilitate an accelerated reaction.

In conjunction with the preparation of the compounds falling within the above Formula III from the salt form of the compounds falling within Formula II, i.e., $R_3$ in each case is a metal ion, it is desirable that the salt form of Formula II compounds be converted to the acid form, i.e., where $R_3$ in each case is hydrogen, prior to the hydrolysis step in order to obtain high conversion yields. (However, converting the salts of Formua II to the acid form is not essential for the production of salts of Formula III.) More specifically, this conversion of the salt form to the acid form is accomplished by passing, for example, an aqueous solution containing the disodium salt of EEDP through a hydrogne ion exchange resin such as those which are commercially available under the trade names Amberlite IR 120 and Dowex 50. The resultant acid form usually having a pH below 4 can be hydrolyzed according to the general process heretofore described.

In conjunction with the over-all hydrolysis of the acid and ester forms of EEDP, it is desirable, after heating in the hydrolysis step, to remove the water from the resulting mass by evaporation, for example, under vacuum, e.g., 1/2 to 760 mm Hg, preferably from 1 to 50 mm Hg., at a temperature of from about −10°C to about 150°C, preferably from about −10°C to about 50°C. Subsequently, a water-immiscible, inert solvent such as benzene, toluene, hexane, heptane, isopropyl ether, or octane, cyclo-hexane and the like, is added to the residue product in the reaction vessel and the resultant mixture is azeotropically distilled at a temperature of from about 50°C to about 140°C until substantially no water is observed in the distillate. The desired product formed can be identitied by standard analyses such as $P^{31}$ and $H^1$ nuclear magnetic resonance (abbreviated herein as NMR), elemental analysis, infra red spectrum and the like, depending upon the particular physical and/or chemical form of the product. It is to be understood that these analytical techniques are also applicable to ascertaining the indentification of any of the compounds falling within the above-described Formula I.

As illustrative of the ethane diphosphonates which can be prepared according to the aforementioned hydrolysis reaction of EEDP, there may be mentioned, without limitation, the following compounds:

1. $H_2C(OH)C(OH)(PO_3H_2)_2$ 1,2 dihydroxy ethane-1,1-diphosphonic acid
2. $H_2C(OH)C(OH)(PO_3NaH)_2$ disodium 1,2 dihydroxy ethane-1,1-diphosphonate
3. $H_2C(OH)C(OH)[PO_3(C_2H_5)_2]_2$ tetraethyl 1,2 dihydroxy ethane-1,1-diphosphonate 4. $H_2C(OH)C(OH)(PO_3HC_6H_5)_2$ diphenyl 1,2 dihydroxy ethane-1,1-diphosphonate
5. $H_2C(OH)C(OH)(PO_3K_2)_2$ tetrapotassium 1,2 dihydroxy ethane-1,1-diphosphonate
6. $H_2C(HO)C(OH)(PO_3Zn)_2$ dizinc 1,2 dihydroxy ethane-1,1-diphosphonate
7. $H_2C(OH)C(OH)(PO_3HC_4H_9)_2$ dibutyl 1,2 dihydroxy ethane-1,1-diphosphonate

AMMONOLYSIS OF EPOXY ETHANE DIPHOSPHONATE

The reaction of the epoxy ethane diphosphonate with a nitrogenous material from the group ammonia or primary and secondary amines (generically described herein as ammonolysis) yields "amine"-hydroxy derivatives according to the following general reaction:

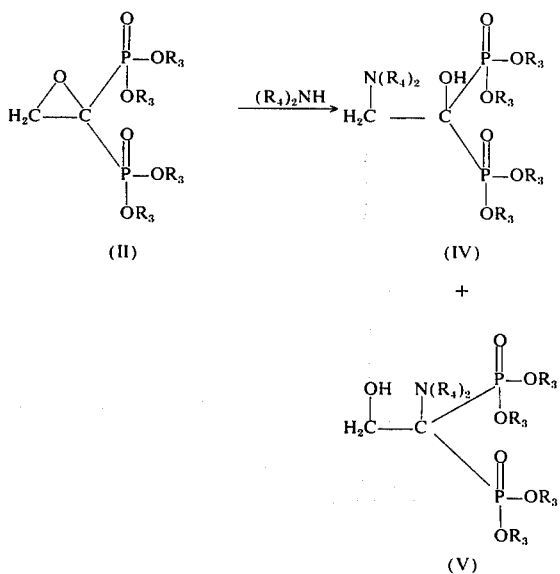

wherein $R_3$ is the same as heretofore defined. In the above reaction, $(R_4)_2NH$ designates ammonia, primary amine or secondary amine, and $R_4$ has the same connotation as heretofore set forth and is from the group hydrogen and alkyl containing from 1 to 30, preferably from 1 to 8, carbon atoms. As shown in the above reaction, a mixture of two isomers (1-amino -2-hydroxy and 2- amino -1-hydroxy ethane diphosphonate) are formed; [the word "amino" is used in this case to designate $-NH_2$ or $-N(R_4)_2$].

It is found in all cases that the major product formed in conjunction with the above reaction is the 2- amino 1-hydroxy ethane diphosphonate. Where one so desires, the isomers can be separated by conventional chromatographic methods. However, it is found that one isomer does not substantially interfere with the other isomer in conjunction with end-use applications and consequently, separation of the two isomers is not necessary. This particular facet of these two isomers is also found to be applicable to the other isomeric mixtures of the ethane diphosphonates described hereinafter.

The above ammonolysis reaction is generally conducted at a temperature between about −40°C and about 150°C, and under atmospheric conditions. However, it is within the scope of the present invention that super-atmospheric, for example from about 1 to about 10 atmospheres, and sub-atmospheric, for example ½ to 760 mm Hg, conditions may be utilized where one so desires. It is preferred in carrying out the aforementioned ammonolysis reaction that the amine be utilized in excess of that stoichiometrically required to react with the epoxy ethane diphosphonate; for example, a mole ratio of 100:1 of ammonia to EEDP permits the ammonia to function also as a reaction medium. Any amount of amine can be used in excess of that stoichiometrically required as long as there is no substantial adverse effect to the formation of the desired end product. In conjunction with the aforementioned reaction and when the starting EEDP is in the ester form, an inert organic solvent such as benzene, toluene, hexane, heptane, halocarbon such as carbon tetrachloride, chloroform, methylene chloride, isopropyl ether, octane, cyclo-hexane and the like may be utilized, where one so desires, in order to, inter alia, facilitate easier handling of the reaction mass, temperaure control, better yields.

In conjunction with the general ammonolysis reaction heretofore shown and specifically where the compounds falling within Formula II are in the acid form (i.e., $R_3$ is hydrogen), the resultant ethane diphosphonate isomeric mixture is in the ammonium salt form and further processing steps are required in order to prepare the desired ethane diphosphonate in the acid form. Specifically, at least stoichiometric quantities of an alkaline earth metal (i.e., barium, strontium, calcium and magnesium) hydroxide, for example, barium hydroxide (in water)) is added to the isomeric mixture and which results in the formation of the barium salts of compounds falling within formulae IV and V. (This is established by elemental analysis of the dry material and by nuclear magnetic resonance, NMR, spectrum of the $P^{31}$ and $H^1$ atoms.) The barium salts are separated from the reaction mixture by the addition of a water-soluble organic solvent such as ethanol, followed by filtration and washing with an inert liquid, non-aqueous organic solvent such as methanol, ethanol, acetone, dimethyl formamide and the like, to remove the residual water. The filter cake which is the barium salt is dried at a suitable temperature (e.g., 10°C to 75°C) in order to remove this solvent and then subsequently slurried with an organic material such as ether. Either a substantially anhydrous sulfuric acid or an aqueous solution thereof (or any mineral acid which will form a salt precipitate with the cation) in an organic material such as ether, is then reacted with the barium salt-ether slurry to form the fully protonated, i.e., acid form, of the ethane diphosphonate and a barium sulfate precipitate. A halohydrocarbon, such as chloroform, is added to the end products to assist the separation of the ethane diphosphonate from the barium sulfate. After stirring to insure complete reaction, the barium sulfate is filtered off the remaining solution is then subjected to low temperature (e.g. from −5°C to 30°C) — low vacuum distillation (e.g. from ½ to 28 mm Hg) to remove the halohydrocarbon. The resultant residue is then subjected to azeotropic drying (i.e., the distillation according to the procedure heretofore mentioned in conjunction with the preparation of the compounds of Formula III) to yield the acid form ($R_3$ is hydrogen) of the compounds falling within Formulae IV and V. This overall procedure to convert the ammonium salt to the fully protonated form is referred to herein as the "alkaline earth metal treatment" for the sake of brevity.

As illustrative of the ethane diphosphonates which can be prepared according to the aforementioned ammonolysis of EEDP, there may be mentioned, without limitation, the following compounds:

8. $H_2C(NH_2)C(OH)(PO_3H_2)_2$ 2-amino-1-hydroxyethane-1,1-diphosphonic acid
9. $H_2C(OH)C(NH_2)(PO_3H_2)$ 2-hydroxy-1-aminoethane-1,1-diphosphonic acid
10. $H_2C(NH_2)C(OH)(PO_3Na_2)_2$ tetrasodium 2-amino-1-hydroxyethane-1,1-diphosphonate
11. $H_2C(NHCH_3)C(OH)(PO_3H)_2$ 2-methylamino-1-hydroxyethane-1,1-diphosphonic acid
12. $H_2C(NHCH_3)C(OH)[PO_3(C_2H_5)_2]_2$ tetraethyl 2-methylamino-1-hydroxyethane-1,1-diphosphonate
13. $H_2C[N(C_2H_5)2]C(OH)(PO_3H_2)_2$ 2-diethylamino-1-hydroxyethane-1,1-diphosphonic acid
14. $H_2C(NH_2)C(OH)[PO_3(C_2H_5)_2]_2$ tetraethyl 2-amino-1-hydroxyethane-1,1-diphosphonate 15. $H_2C[NC_4H_9)_2]C(OH)(PO_3Zn)_2$ dizinc 2-dibutylamino-1-hydroxyethane-1,1-diphosphonate
16. $H_2C(NH_2)C(OH)(PO_3HC_4H_9)_2$ dibutyl 2-amino-1-hydroxy ethane-1,1-diphosphonate

REACTION OF EPOXY ETHANE DIPHOSPHONATE WITH ACIDS

The reacton of the epoxy ethane diphosphonates with an acid having the generic formula HZ (hereinafter defined) yields a variety of ethane diphosphonates according to the following reaction:

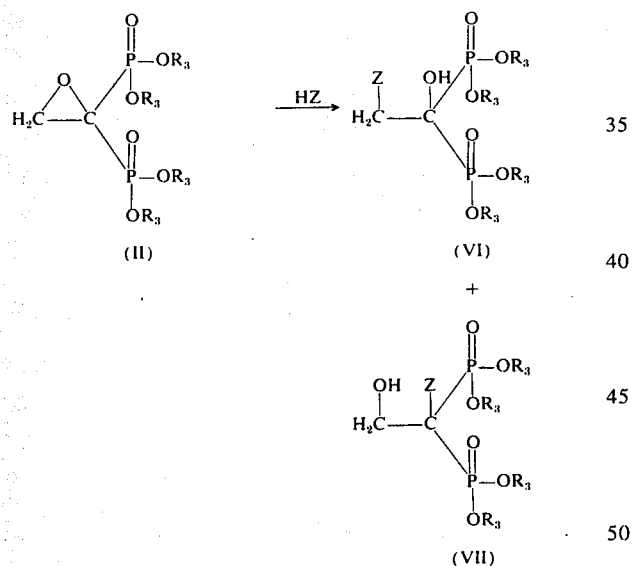

In the above reaction, HZ designates certain inorganic and organic acids. Specifically, the cation, Z, is from the group halogen (such as chlorine, bromine, fluorine and the like), —CN, acetoxy ($CH_3COO—$), sulfonate (—$SO_3R_4$ wherein $R_4$ has the same connotation as heretofore set forth and is from the group hydrogen and alkyl), benzoyl ($C_6H_5CO—$), and carboxy (HOOC—).

As shown in the above reaction, a mixture of two isomers are formed. It is found in all cases that the major products formed are those compounds falling within the above Formula VI, i.e., in which the hydroxy group is attached to the carbon containing the two phosponate groups.

The above-described acid reaction is generally conducted at a temperature between about −10°C and 150°C, preferably between about 0°C and 100°C. It is to be understood that the above acid reaction can be carried out under atmospheric conditions, superatmospheric (e.g. 1 to 10 atmospheres), and subatmospheric (e.g. ½ to 760 mm Hg) conditions; however, it is preferred that the acid reaction be carried out under atmospheric conditions.

While the above-described acid reaction may be carried out utilizing stoichiometric amounts of the epoxy ethane diphosphonate and said acid, i.e. HZ, it is preferred that the acid, HZ, be utilized in excess of that stoichiometrically required to react with the epoxy ethane diphosphonate. For exemplary purposes only, a mole ratio of from about 2:1 to about 10:1 (i.e., excess of acid) in carrying out the foregoing reaction is found desirable. It is also within the scope of the present invention that the acid reaction, where one so desires, may be carried out in the presence of an inert solvent such as an alcohol (for example methanol and ethanol), ethers (e.g. tetrahydrofuran and ethyl ether), and a halocarbon such as chloroform, and carbon tetrachloride, in order, inter alia, to facilitate easier handling of the reaction mass, temperature control and the like.

As illustrative of the ethane diphosphonates which can be prepared according to the aforementioned acid reaction with EEDP, there may be mentioned, without limitation, the following compounds:

17. $H_2C(Cl)C(OH)(PO_3H_2)_2$ 2-chloro-1-hydroxyethane-1,1-diphosphonic acid
18. $H_2C(OH)C(Cl)(PO_3H_2)_2$ 2-hydroxy-1-chloroethane-1,1-diphosphonic acid
19. $H_2C(CN)C(OH)(PO_3KH)_2$ dipotassium 2-cyano-1-hydroxyethane-1,1-diphosphonate
20. $H_2C(OOCCH_3)C(OH)(PO_3HC_2H_5)_2$ diethyl 2-acetoxy-1-hydroxyethane-1,1-diphosphonate
21. $H_2C(SO_3H)C(OH)(PO_3H_2)_2$ 2-sulfo-1-hydroxyethane-1,1-diphosphonic acid
22. $H_2C(OCC_6H_5)C(OH)(PO_3HC_6H_5)_2$ diphenyl 2-benzoyl-1-hydroxyethane-1,1-diphosphonate
23. $H_2C(F)C(OH)(PO_3HNa)_2$ disodium 2-fluoro-1-hydroxyethane-1,1-diphosphonate
24. $H_2C(SO_3C_2H_5)C(OH)(PO_3H_2)_2$ 2-ethylsulfo-1-hydroxyethane-1,1-diphosphonic acid
25. $H_2C(Br)C(OH)[PO_3(C_4H_9)_2]_2$ tetrabutyl 2-bromo-1-hydroxyethane-1,1-diphosphonate
26. $H_2C(CN)C(OH)[PO_3(CH_3)_2]_2$ tetramethyl 2-cyano-1- hydroxyethane-1,1-diphosphonate

REACTION OF EPOXY ETHANE DIPHOSPHONATE WITH REACTIVE METHYLENE GROUPS

The reaction of the epoxy ethane diphosphonate with a malonate (hereinafter defined) yields of a variety of ethane diphosphonates according to the following reaction:

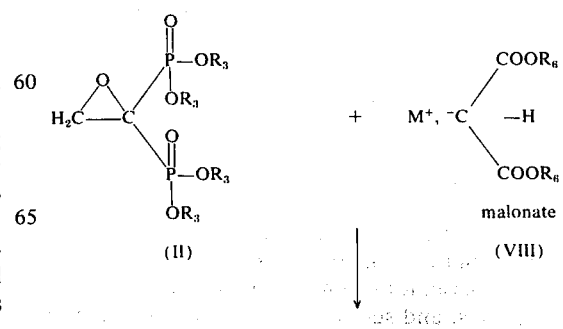

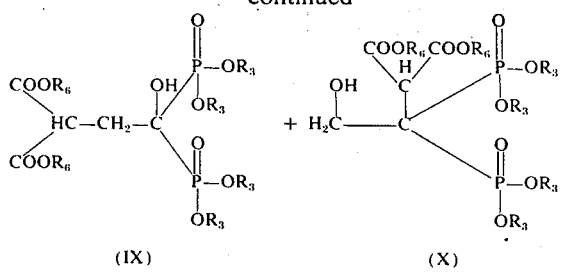

(IX)  (X)

In the above reaction, the malonate, Formula VIII, has a metallic cation, $M^+$, attached to the middle carbon atom, and M is preferably an alkali metal cation such as sodium, lithium, or potassium. $R_6$ in the malonate Formula VIII has the same connotation as heretofore set forth and is an alkyl group containing from 1 to 30 carbon atoms, preferably lower alkyl containing 1 to 8 (more preferably 1 to 4) carbon atoms. As shown in the above reaction, a mixture of the two isomers (Formulae IX and X) are formed. It is found in all cases that the major products formed are the compounds falling within Formula IX, i.e., wherein the hydroxy group is attached to the carbon atom which has the two phosphonyl groups.

The above malonate-epoxy reaction is generally conducted at a temperature between about 5°C and about 240°C, preferably from about 10°C and about 140°C, and under atmospheric conditions. However, it is within the scope of the present invention that super-atmospheric (e.g., 1 to 10 atmospheres) and sub-atmospheric (e.g., ½ to 760 mm Hg) conditions may be utilized where one so desires. While the above-described malonate-epoxy reaction may be conducted by utilizing stoichiometric quantities of both reactants, it is within the scope of the present invention that excess quantities of the malonate can be utilized where one so desires. Furthermore, an inert solvent such as ether (such as isopropyl ether and n-butyl ether), tetrahydrofuran, benzene or toluene may also be utilized where one so desires in order to, inter alia, facilitate easier handling of the reaction mass, control reaction temperatures, and the like.

In conjunction with the preparation of the compounds falling within the above Formulae IX and X from the salt and acid forms of the compounds falling within Formula II, it is desirable that both the salt and acid forms of the Formula II compounds be converted to the ester form, i.e., where $R_3$ is an organic group, prior to the reaction with the malonate. More specifically, the conversion of the salt form to the acid form (Formula II), for example, by undergoing the aforementioned "alkaline earth metal hydroxide treatment" or by passing, for example, an aqueous solution containing the salt of EEDP through a hydrogen ion exchange resin such as those which are commercially available under the trade names Amberlite IR 120 and Dowex 50. The resultant acid form then can be converted to the ester form by the procedure outlined by a S. J. Fitch in the Journal of the American Chemical Society, Vol. 86, pages 61–64, January, 1964, and which procedure is incorporated herein by reference. The resultant esters of compounds falling within Formula II are converted via the "de-oxiranization" procedure immediately set forth above to compounds falling within Formulae IX and X wherein $R_3$ is an organic group, i.e. the ester form. The salts and acids of Formula IX and X can be obtained respectively by reacting the ester with a mineral acid (i.e. acid hydrolysis) and then reacting the acid with a metal hydroxide solution to form a salt.

As illustrative of the ethane diphosphonates which can be prepared according to the aforementioned malonate reaction with EEDP, there may be mentioned, without limitation, the following compounds:

27. $HC(COOC_2H_5)_2CH_2C(OH)(PO_3H_2)_2$ diethyl(2-hydroxy-2,2-diphosphonoethyl) malonate
28. $H_2C(OH)C(PO_3H_2)_2CH(COOC_2H_5)_2$ diethyl (2-hydroxy-1,1-diphosphonoethyl) malonate
29. $HC(COOC_4H_9)_2CH_2C(OH)(PO_3H_2)_2$ dibutyl (2-hydroxy-2,2-didphosphonoethyl) malonate
30. $H_2C(OH)C(PO_3Na_2)_2CH(COOCH_3)_2$ dimethyl (tetrasodium 2-hydroxy-2,2-diphosphonoethyl) malonate
31. $H_2C(COOCH_3)_2CH_2C(OH)(PO_3H_2)_2$ dimethyl(2-hydroxy-2,2-diphosphonoethyl) malonic acid
32. $HC(COOC_2H_5)_2CH_2C(OH)[PO_3(C_2H_5)_2]_2$ diethyl (tetraethyl 2-hydroxy-2,2-diphosphonoethyl) malonate

REACTION OF EXPOXY ETHANE DIPHOSPHONATE WITH ALCOHOLS AND MERCAPTANS

The reaction of the epoxy ethane diphosphonate with certain alcohols and mercaptans generically designated as $R_5XH$ (hereinafter defined) yield a variety of ethane diphosphonates according to the following reaction:

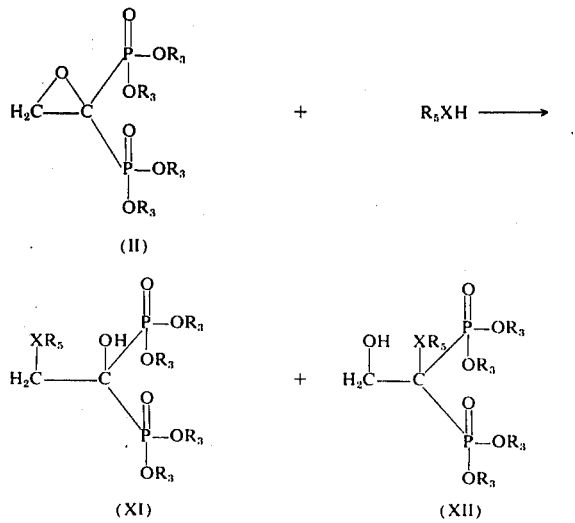

(II)

(XI)  (XII)

In the above reaction, $R_5XH$ generically designates an alcohol or a mercaptan; X is from the group sulfur and oxygen and $R_5$ has the same connotation as heretofore set forth and is from the group alkyl containing 1 to 30, preferably lower alkyl containing from 1 to 8, carbon atoms, $C_6H_5$ (phenyl) and $CH_2C_6H_5$ (benzyl). As shown in the above reaction, a mixture of two isomers is formed. It is found in all cases that the major product formed is a compound falling within Formula XI, i.e., wherein the hydroxy group is attached to the carbon atom containing the two phosphonyl groups.

The above reaction between the epoxy ethane diphosphonate and the alcohol or mercaptan is generally conducted at a temperature between 5°C and 180°C, preferably from about 10°C and 100°C, and under atmospheric conditions. However, it is within the scope of the present invention that super-atmospheric (e.g. 1 to 10 atmospheres) and sub-atmospheric (e.g. ½ to 760 mm Hg) conditions may be utilized where one so desires.

In conducting the aforementioned reaction, it is desirable to utilize a metallic material such as metallic sodium or lithium or potassium (in at least stoichiometric amounts) or an acid catalyst (generally in less than stoichiometric amounts) such as those materials heretofore defined. While the aforementioned reaction may be carried out utilizing stoichiometric quantities of both the epoxy ethane diphosphonate and the alcohol or mercaptan, excess quantities in any amounts of the aforesaid alcohols or mercaptans may be utilized where one so desires as long as there are not substantial adverse effects in producing the desired product.

The alcohols utilized are the monoatomic aliphatic alcohols containing from 1 to 30 carbon atoms, preferably from 1 to 8 carbon atoms, incuding the respective isomers thereof. Typcial alcohols include, for example, methanol, ethanol, propanol and n-butyl alcohol. It is also within the scope of this invention to utilize alcohols such as phenol and benzyl alcohol.

The mercaptans utilized are the aliphatic mercaptans containing from 1 to about 30 carbon atoms, preferably from 1 to 8 carbon atoms, and include, for exemplary purposes only, methyl mercaptan, ethyl mercaptan, propyl mercaptan and n-butyl mercaptan. The isomers of the varous mercaptans are also included within the present invention.

In conjunction with the preparation of the compounds falling within the above Formula XI and XII from the salt and acid forms of the compounds falling within Formula II, it is desirable that both the salt and acid forms of the Formula II compounds be converted to the ester form, i.e., where $R_3$ is an organic group, prior to the reaction with the particular alcohol or mercaptan. This conversion of the salt and acid forms to the ester form is accomplished according to the same procedure outlined heretofore in conjunction with the EEDP-malonate process reaction.

As illustrative of the ethane diphosphonates which can be prepared according to the aforementioned reaction of EEDP with either alcohols or mercaptans, there may be mentioned, without limitation, the following compounds:

33. $H_2C(OCH_3C(OH)$ $(PO_3H_2)_2$ 2-methoxy -1-hydroxy ethane-1,1-diphosphonic acid
34. $H_2C(OH)C(OCH_3)$ $(PO_3H_2)_2$ 2-hydroxy -1-methoxy ethane-1,1-diphosphonic acid
35. $H_2C(OC_2H_5)C(OH)$ $(PO_3NaH)_2$ disodium 2-ethoxy -1-hydroxy ethane-1,1-diphosphonate
36. $H_2C(SCH_3)C(OH)$ $(PO_3H_2)_2$ 2-thiomethyl -1-hydroxy ethane-1,1-diphosphonic acid
37. $H_2C(SC_2H_5)C(OH)[PO_3(C_6H_5)_2]_2$ tetraphenyl 2-thioethyl -1-hydroxy, ethane-1,1-diphosphonate.
38. $H_2C(OCH_3)C(OH)$ $(PO_3HC_4H_9)_2$ dibutyl 2-methoxy -1-hydroxy ethane-1,1-diphosphonic acid
39. $H_2C(SCH_3)C(OH)$ $(PO_3HCH_3)_2$ dimethyl 2-thiomethyl, 1-hydroxy ethane-1,1-diphosphonic acid
40. $H_2C(OC_6H_5)C(OH)$ $(PO_3H_2)_2$ 2-phenoxy -1-hydroxy ethane-1,1-diphosphonic acid
41. $H_2C(OC_6H_5)C(OH)$ $(PO_3HC_2H_5)_2$ diethyl 2-phenoxy -1-hydroxy ethane-1,1- diphosphonic acid
42. $H_2C(SC_6H_5)C(OH)$ $(PO_3H_2)_2$ 2-thiophenyl, 1-hydroxy ethane-1,1-diphosphonic acid

ACID CATALYZED REARRANGEMENT OF EPOXY ETHANE DIPHOSPHONATES

The reaction of the epoxy ethane diphosphonate in the presence of a metal halide Lewis acid which functions as an acid catalyst yields the oxy derivative of the epoxy ethane diphosphonate according to the following reaction:

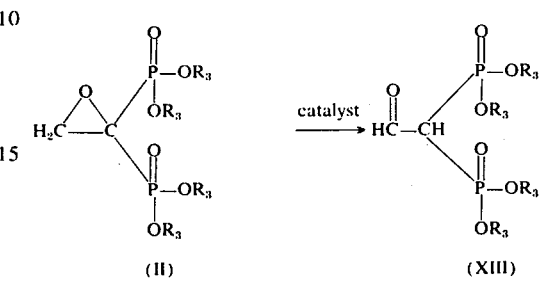

In conjunction with the above-described reaction, a wide variety of metal halide Lewis acids can be utilized in order to effect an acid catalyzed rearrangement of the epoxy ethane diphosphonate. There may be mentioned for exemplary purposes only and without any limitation metal halide Lewis acids such as boron trifluoride, zinc chloride, magnesium bromide, ferric chloride, stannic chloride, titanium chloride, zirconium chloride, aluminum chloride and the like. In conjunction with the utilization of the Lewis acid for the acid catalyzed rearrangement, it is preferred to first dissolve or suspend the metal halide in a non-aqueous inert aprotic solvent such as nitromethane, dichloromethane, nitrobenzene, nitropropane, chlorobenzene, dichlorobenzene, dichloroethane, tetrachloroethane, perchloroethylene, petroluem ether, carbon tetrachloride, chloroform, carbon disulfide, ethyl ether, benzene and the like, and then contact the resultant solution or slurry with the EEDP material. The amount of solvent utilized is not a limiting factor as long as that amount chosen dose not substantially adversely affect the preparation of the desired end product.

The acid catalyzed rearrangement of the epoxy ethane diphosphonate is generally conducted with the epoxy ethane diphosphonate and a Lewis acid catalyst (and, if desired, an inert aprotic solvent such as ethyl ether) at a temperature between about −20°C and 150°C, and under atmospheric conditions. Higher or lower temperatures can be utilized, e.g., as low as −50°C and as high as 250°C, depending, for example, upon the boiling point of said solvent. It is within the scope of the present invention that super-atmospheric (e.g., from about 1 to 10 atmospheres) and sub-atmospheric (e.g. ½ to 760 mm Hg) conditions and also in an inert atmosphere such as nitrogen or helium may be utilized where one so desires.

The quantity of Lewis acid catalyst utilized in conjunction with the acid catalyzed rearrangement will vary somewhat, depending upon the type of metal halide Lewis acid catalyst utilized, the temperature at which the reaction takes place, and, in some instances, the pressure of the system. It is to be understood that any amount of Lewis acid catalyst can be utilized as long as that amount is not substantially detrimental to achieving the desired end product. It is found that from about 0.01 to about 4 mole equivalents of said catalyst for each mole of EEDP starting material suffices to form the aforesaid "oxy" derivative in satisfactory yields.

As illustrative of the ethane diphosphonates which can be prepared according to the aformentioned acid catalyzed rearrangement of EEDP, there may be mentioned, without limitation, the following compounds:

43. HC(O)C(H) (PO$_3$H$_2$)$_2$ 2-oxy ethane-1,1-diphosphonic acid
44. HC(O)C(H) (PO$_3$NaH)$_2$ disodium 2-oxy ethane-1,1-diphosphonate
45. HC(O)C(H)[PO$_3$(C$_2$H$_5$)$_2$]$_2$ tetraethyl 2-oxy ethane-1,1-diphosphonate
46. HC(O)C(H) (PO$_3$HC$_6$H$_5$)$_2$ diphenyl 2-oxy ethane-1,1-diphosphonate
47. HC(O)C(H) (PO$_3$K$_2$)$_2$ tetrapotassium 2-oxy ethane-1,1-diphosphonate
48. HC(O)C(H) (PO$_3$HCH$_3$)$_2$ dimethyl 2-oxy ethane-1,1-diphosphonate

CYANIDE REACTION WITH EPOXY ETHANE DIPHOSPHONATES

An alternative process for preparing the cyano and carboxy derivatives from epoxy ethane diphosphonate, the reaction respectively of an alkali cyanide, generically designated MCN (hereinafter described), and the subsequent hydrolysis of the resulting product proceeds according to the following general reaction:

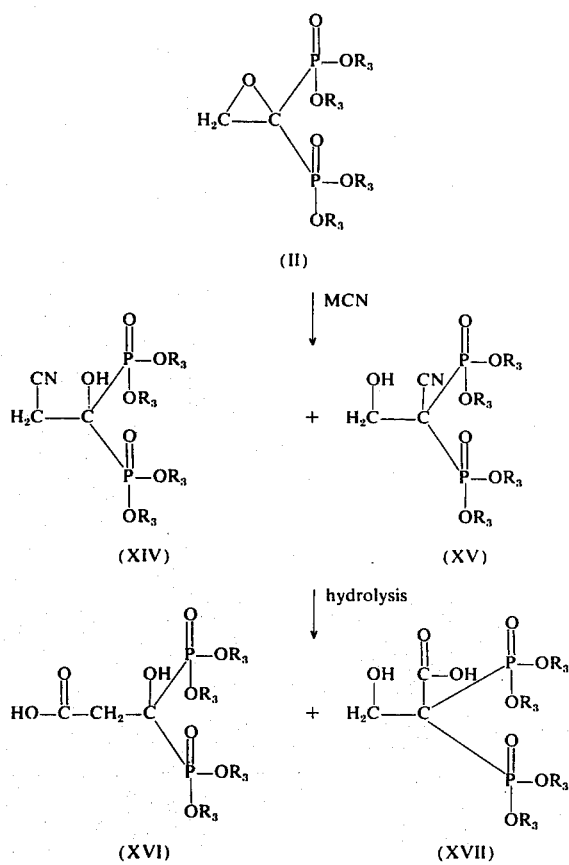

In the above reaction, specifically with the utilization of MCN, M represents an alkali metal cation preferably sodium, lithium or potassium. As shown in the above reactions, a mixture of two isomers are formed in each case, and the major product formed is the compound falling within Formula XIV or XVI, i.e., wherein the hydroxy group is attached to the carbon atom containing the two phosphonyl groups.

The above alkali cyaninde-epoxy reaction is generally conducted at a temperature between about $-10°C$ and $150°C$, preferably between about $0°C$ and $100°C$, and under atmospheric conditions. However, it is within the scope of the present invention that superatmospheric (e.g., 1 to 10 atomspheres) and subatmospheric (e.g., ½ to 760 mm Hg) conditions may be utilized where one so desires.

While the above-described cyanide-epoxy reaction is generally carried out with the utilziation of stoichiometric quantities of both reactants, it is also within the scope of the present invention to utilize excess quantities of the cyanide material. For exemplary purposes only, a mole ratio of from about 1.1:1 to about 10:1 (i.e., excess MCN) in carrying out this reaction is preferred.

It is to be understood that a combination and concurrent use of the double salts of the cyanide, for example, sodium and potassium cyanide (NaCN and KCN) can be utilized in order to prepare the compounds falling within the Formulae XIV and XV. These new compounds then can be utilized as such or act as chemical intermediates for the formation of additional derivatives of the ethane diphosphonates as shown in the above Formulae XVI and XVII, i.e., where the two isomers having the —CN substituent are hydrolyzed to form a mixture of two isomers having carboxy groups in place of the cyanide groups. This hydrolysis may be carried out in any conventional manner, for example, by mixing the cyanide isomeric mixture with an aqueous solution containing from about 1% to about 60% by weight of a mineral acid such as hydrochloric acid or sulfuric acid and then heating (e.g., 50°C to 150°C) under reflux conditions for a sufficient period of time, for example, from about thirty minutes to about two hours or more, in order to yield the "carboxy" isomeric mixture of Formulae XVI and XVII.

In accordance with the processes heretofore described in the "de-oxiranization" of the epoxy ethane diphosphonate falling within Formula II, it is to be understood that the resultant ethane diphosphonate products, whether they be an isomeric mixture or a single compound, may be isolated from the resultant reaction mass through the use of conventional techniques such as solvent extraction, evaporization, centrifugation or the like, and further purified, if necessary, through re-crystallization, chromatography or the like. In the case of the production of the isomeric mixtures heretofore mentioned, conventional selective chromatographic techniques can be utilized where one so desires to obtain a single isomer such as those described in Canadian patent 812,741 which is incorporated herein by reference. However, in conjunction with the utility of the ethane diphosphonates, it is found that one isomer does not substantially interfere with the other isomer, and consequently separation of the two isomers is not necessary.

The aforedescribed new processes of "de-oxiranization" are unique in preparing the new and useful organophosphorus compounds, i.e., the ethane diphosphonates of the present invention, since these processes, inter alia, represent an inexpensive method to manufacture said ethane diphosphonates, control reaction conditions, and produce high yields.

The acid and salt forms of the ethane diphosphonates falling within Formula I of the present invention have unique utility in the field of treating water or aqueous systems and function as both a sequestering agent and as a "threshold" agent. It is to be understood that the term "threshold" as utilized herein refers to the chemical and/or physical phenomenon that less than stoichiometric quantities of the particular ethane diphosphonate can effectively prevent the precipitation of various metallic ions such as calcium, iron, copper and cobalt. In other words, the "threshold" treatement of water is that technique by means of which less than stoichiometric quantities of the treating agent are added to interfere with the growth of crystal nuclei and thereby prevent the deposition of insoluble deposits. The term is applied, for example, to the treatment of water with polyphosphates and is discussed in references such as U.S Pat. No. 2,038,316, and the article by Reitmeir and Buehrer in the Journal of Physical Chemistry, Vol. 44, pages 535 to 574 (1939). An additional explanation of the threshold effect will be found in the publications of Hatch and Rice appearing in Industrial Engineering and Chemistry of January, 1939, and August, 1945. All of the aforementioned publications are to be considered as incorporated herein by reference.

The acid and ester forms of the ethane diposponates falling within Formula I have unique utility in the field of flame retardancy for cellulosic materials and specifically function as flame retardants therefor.

In addition to the end-use applications set forth immediately above, the ethane diphosphonates of the present invention represent new, unique organo-phosphorus structures which also can function as chemical intermediates in order to prepare other materials. In other words, the ethane diphosphonates react with various organic and/or inorganic materials to form a variety or derivatives thereof, due to the fact that the substituents on the carbon atoms of the ethane portion, in addition to the phosphonyl groups, represent highly reactive radicals or difunctional groups and can be removed therefrom and/or coupled with other organic or inorganic radicals.

The following examples are presented to illustrate the invention, with parts and percentages by weight being used in the examples unless otherwise indicated.

EXAMPLE I

Into a reaction vessel equipped with a thermometer, mechanical stirrer and reflux condenser are charged 102 grams of EEDP acid and 500 milliliters of water. The resultant slurry is heated to 90°C and maintained at this temperature for approximately three hours. At the end of this time a solution is formed and the water in the solution is evaporated under vacuum, ½ mm Hg, until a tacky material is formed. Approximately 500 milliliters of benzene is then added to the tacky material in the reaction vessel, and the resultant slurry is azeotropically distilled at a temperature of 80°C, utilizing a reflux condenser equipped with a Dean Starke trap, until no water is observed in the distillate collected in the aforementioned trap. $P^{31}$ and $H^1$ NMR analyses show that 1,2dihydroxy ethane-1,1-diphosphonic acid (herein designated as compound No. 1) is produced.

EXAMPLE II

Approximately 102 grams of disodium salt of EEDP (heretofore described as compound No. 2) contained in 500 milliliters water is passed through a column of a strong cation exchange resin at an average rate of 130 grams per minute. This column, which is 2 inches in diameter and 34 inches high, conists of water insoluble beads of the hydrogen or acid form of a strong cation exchange resin, which is commercially available under the trademark "Dowex 50", consisting of water insoluble beads of a copolymer of styrene-AR-ethyl-vinyl benzene and divinyl benzene and which copolymer contains nuclear sulfonic acid groups and which co- polymer is described in Vol. 69, pages 28–30, of the Journal of the American Chemical Society (which is incorporated herein by reference), having a capacity of 4.25 milligram equivalents per gram. The aqueous solution containing EEDP is allowed to pass through said column until a composite effluent from the column has a pH of about 1.0 (glass electrode) and which composite effluent is essentially free of sodium ions. This composite effluent is an aqueous solution containing EEDP in the acid form. This EEDP acid in solution is then subjected to the same process as described in Example I, and the aforementioned 1,2-dihydroxy-ethane-1,1-diphosphonic acid is produced. The disodium salt of 1,2-dihydroxy ethane-1,1 -diphosphonic acid is obtained by reacting two molar equivalents of NaOH (in solution) with one molar equivalent of said acid. $P^{31}$ and $H^1$ NMR and elemental analyses show the formation of disodium 1,2-dihydroxy ethane-1,1-diphosphonate following the procedure immediately set forth above. The tetrapotassium salt (designated as compound No. 5 herein) is prepared by reacting four molar equivalents of KOH with one molar equivalent of said acid. The dizinc salt (designated as compound No. 6 herein) is prepared by reacting two molar equivalents of solid $Zn(OH)_2$ with one molar equivalent of said acid. The tetraethyl ester (designated as compound No. 3 herein) is formed by reacting four molar equivalents of triethyl orthoformate with one molar equivalent of said acid. The triethyl and monoethyl esters of said acid are also prepared by hydrolyzing the tetraethyl ester in $H_2SO_4$ as is shown by $P^{31}$ and $H^1$ NMR, elemental analyses and infra red analysis of reaction samples taken at different time levels during the aforementioned $H_2SO_4$ hydrolysis. In other words, the tetraethyl ester is first formed by the reaction of the triethyl orthoformate with said acid. During the subsequent acid hydrolysis, esters groups are removed to form the triethyl ester, the diethyl ester, the monoethyl ester, and the acid per se if hydrolysis proceeds to completion. Other total esters and partial esters (i.e., butyl, propyl, etc.) are prepared by utilizing the appropriate trialkyl formate.

EXAMPLE III

Approximately one hundred grams of the tetraethyl ester of EEDP (having the structure of Formula II wherein $R_3$ in all cases is $C_2H_5$), 500 milliliters of water and 50 milliliters of a 5% by weight HCl solution are charged into the reaction vessel described heretofore in Example I. The resultant mixture is heated for approximately four hours at 90°C and then subjected to evaporation at 50°C under vacuum (10 mm Hg) for a period of approximately 85 minutes in order to remove substantially all the water. The resultant material in the reaction vessel is a liquid oily-type mass. Approximately 500 milliliters of benzene is added to this liquid oily mass and the resultant mixture is subjected to azeotropic distillation in order to remove all water from the system as described in conjunction with Example I heretofore set forth. This azeotropic distillation (80°C) takes place over a period of approximately one hour and the analysis by $P^{31}$ and $H^1$ NMR and elemental analyses show that tetraethyl, 1,2-dihydroxy ethane diphosphonate, having the structural formula shown in the Abstract (also designated compound No. 3 herein), is formed.

EXAMPLE IV

Into a conventional round-bottom reaction vessel equipped with a dry-ice condenser and mechanical stirrer and containing approximately 100 grams of EEDP acid is charged, dropwise, liquid ammonia which has been condensed at −50°C by passing gaseous ammonia from a conventional storage cylinder through the aforementioned dry-ice condenser. This addition of the liquid ammonia to the EEDP takes place over a period of approximately three hours, with continuous stirring, in order to yield a mole ratio of ammonia to EEDP acid of 10:1. At the end of three hours the dry-ice condenser is removed and the unreacted ammonia is distilled off by slowly heating the contents of the reaction vessel to approximately 20°C. $P^{31}$ and $H^1$ NMR and elemental analyses show that there is produced two isomers, in the ammonium salt form, having the following formula:

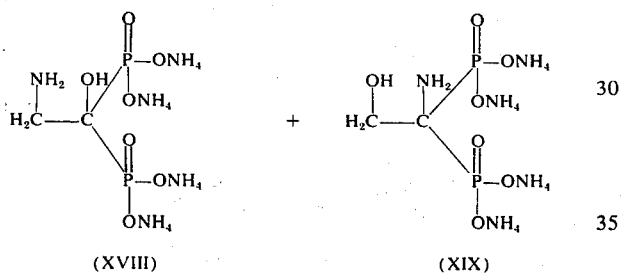

The pure acid forms of the isomeric mixture of the ethane diphosphonates of Formulae XVIII and XIX are obtained in the following manner. First, the isomeric mixture is reacted with stoichiometric amounts of barium hydroxide (in water). The barium-containing isomeric product is then separted from the reaction mixture by the addition of 500 milliliters of ethanol followed by filtration and washing with three separate portions of 100 milliliters of acetone in order to remove the residual water. The filter cake which is the barium-containing isomeric mixture, is dried in a drum dryer for 38 minutes at a temperature of approximately 75°C. The dried material is subsequently slurried with 500 milliliters of ether; 250 milliliters of ether containing 50 grams of anhydrous $H_2SO_4$ is added to said slurry in order to form the fully protonated ammonia containing ethane diphosphonate and a barium sulfate precipitate. Approximately 200 milliliters of chloroform is added to the end product in order to aid in the separation of the aforementioned fully protonated acid from the barium sulfate. After stirring to insure complete reaction, the barium sulfate is filtered off and the remaining solution is subjected to evaporation at low temperature (20°C) vacuum distillation (7 mm Hg) to form a tacky material which is then subjected to azeotropical distillation using benzene as the solvent. $P^{31}$ and $H^1$ NMR and elemental analyses show that the ethane diphosphonates, heretofore described as compounds Nos. 8 and 9, are formed.

EXAMPLE V

Following the procedure outlined in the above Example IV, the ammoniated form of the tetraethyl ester of ethane diphosphonate is prepared, with the exception that no intermediate $NH_4^+$ salt is formed, and thus the barium hydroxide "treatment"is eliminated. The starting material is the tetraethyl epoxy ethane diphosphonate. After the addition of the ammonia, $P^{31}$ and $H^1$ NMR and elemental analyses show the formation of two isomers having the formulae

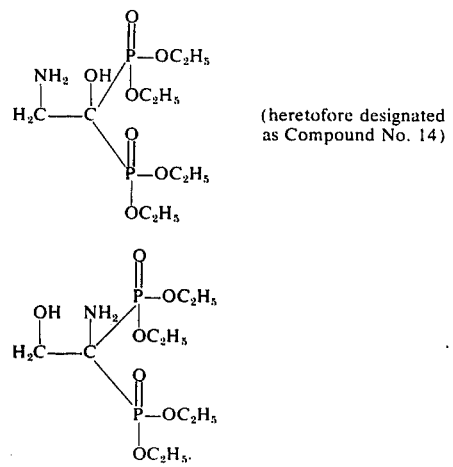

(heretofore designated as Compound No. 14)

EXAMPLE VI

Methylaminohydroxyethane diphosphonic acid is prepared according to the process described in the aforemetioned Example V by substituting methylamine gas for the ammonia gas. Chemical analysis shows the formation of an isomeric mixture having formulae $H_2C(NHCH_3)C(OH)[PO_3(C_2H_5)_2]_2$ and $H_2C(OH)C(NHCH_3)[PO_3(C_2H_5)_2]_2$. EXAMPLE VII Diethylaminohydroxyethane diphosphonic acid is prepared according to the procedure outlined in Example V with the exception that diethylamine replaces the ammonia gas and the dry-ice condenser is replaced with a water-cooled condenser. $P^{31}$ and $H^1$ NMR and elemental analyses show the formation of two isomers having the formulae $H_2C[NC_2H_5)_2]C(OH)-[PO_3(C_2H_5)_2]_2$ and $H_2C(OH)C[N(C_2H_5)_2][PO_3(C_2H_5)_2]_2$.

EXAMPLE VIII

Into a reaction vessel such as that described in Example I are charged 100 grams of EEDP acid and 500 milliliters of carbon tetrachloride. The reaction vessel is immersed in an ice bath in order to maintain the temperature of the contents therein at approximately 5°C. Over a period of approximately six hours and with continuous stirring, hydrogen chloride gas is bubbled into the EEDP solution at a rate in order to have a final mole ratio of HCl to EEDP acid of 10:1. At the end of six hours, the resultant solution is evaporated at 85°C to dryness. $P^{31}$ and $H^1$ NMR and elemental analyses show the formation of two isomers having the formulae $H_2C(Cl)C(OH)(PO_3H_2)_2$ and $H_2C(OH)C(Cl)-(PO_3H_2)_2$, herein designated, respectively, as compound Nos. 17 and 18.

Example VIII is repeated with the exception that 120 grams of glacial acetic acid is utilized in place of the hydrogen chloride gas and is mixed all at one time with the EEDP acid contained in the carbon tetrachloride solution without the aid of the ice bath. $P^{31}$ and $H^1$ NMR and elemental analyses show the formation of two isomers having the formulae $H_2C(OOCCH_3)C(OH)(PO_3H_2)_2$ and $H_2C(OH)C(OOCCH_3)(PO_3H_2)_2$. The ethyl and butyl esters of these isomers are prepared according to the procedure outlined in the last paragraph of Example II.

EXAMPLE X

Into a reaction vessel such as that described in Example I are charged 100 grams (0.38 moles) of the tetra methyl ester of EEDP, 450 milliliters of acetonitrile and 23 grams (0.40 mol) of sodium potassium cyanide. The resultant mass is then heated at reflux (approximately 75°C) for a period of approximately 20 hours with stirring. Samples taken from the subsequently cooled (20°C) mixture show, via $P^{31}$ and $H^1$ NMR and elemental analyses, the formation of $H_2C(CN)C(OH)[PO_3(CH_3)_2]_2$ (herein designated as compound No. 26) and traces of $H_2C(OH)C(CN)[PO_3(CH_3)_2]_2$. The phenyl, ethyl, and butyl partial and full esters of these isomers are prepared according to the above procedure by utilizing as a starting material the respective ester of EEDP. The sodium, potassium and zinc salts of these isomers are prepared, respectively, by first subjecting the aforesaid esters to complete or partial acid hydrolysis followed by reacting stoichiometric quantities of the isomeric acid form mixture with, individually, an aqueous solution of sodium, potassium and zinc hydroxide.

EXAMPLE XI

Into a reaction vessel such as that described in Example I are charged 50 grams of the acid form of EEDP and 150 milliliters of 95% $H_2SO_4$. The resultant mass is then heated at 80°C for a period of approximately 5 minutes with intermittent stirring. $P^{31}$ and $H^1$ NMR and elemental analyses show the formation of 2-sulfo, 1-hydroxy ethane-1,1-diphosphonic acid (herein designated as compound No. 21) and 2-hydroxy-1-sulfoethane-1,1-diphosphonic acid. The sodium, magnesium and zinc salts of these isomers are prepared, respectively, by reacting the isomeric mixture with 100% excess stoichiometric quantities of the respective metal hydroxide solution in order to form said salts.

EXAMPLE XII

Into a reaction vessel such as that described in Example I are charged 75 grams of the diphenyl ester of EEDP and 150 grams of benzoic acid dissolved in 500 milliliters of ethyl ether. The resultant mass is then refluxed (35°C) for a period of approximately 2 hours. $P^{31}$ and $H^1$ NMR and elemental analyses show the formation of an isomeric mixture of $H_2C(OCC_6H_5)C(OH)(PO_3HC_6H_5)_2$ and $H_2C(OH)C(OCC_6H_5)(PO_3HC_6H_5)_2$.

EXAMPLE XIII

Into a reaction vessel such as that described in Example I are charged 23 grams (1 mole) of sodium metal in 200 milliliters of dry tetrahydrofuran. The reaction vessel is immersed in an ice bath in order to maintain the temperature of the contents therein at approximately 5°C. Approximately 160 grams (1 mole) of ethyl malonate are then slowly added over a period of five minutes to the reaction vessel. Into said reaction vessel are charged dropwise approximately 300 grams (0.95 mole) of the tetraethyl ester of EEDP, and the resultant mass is refluxed (65°C) for ten hours. The reaction mass is cooled to 10°C via an ice bath and 37 grams of HCl is added over five minutes with continuous stirring. The NaCl precipitates and is removed by filtration. The filtrate is subjected to a low temperature (15°C) — low vacuum (10 mm Hg) distillation to remove the solvent and the resultant mass is analyzed. $P^{31}$ and $H^1$ NMR and elemental analyses show the formation of $HC(COOC_2H_5)_2CH_2C(OH[PO_3(C_2H_5)_2]_2$ and gas chromatography shows a trace amount of $H_2C(OH)C[PO_3(C_2H_5)_2]_2CH(COOC_2H_5)_2$. The phenyl, methyl and butyl esters of these isomers are prepared, respectively, by reacting at least stoichiometric quantities of phenyl malonate, methyl malonate and butyl malonate with the full or complete phenyl, methyl, ethyl or butyl ester of EEDP according to the procedure set forth above in Example XIII. In each case an isomeric mixture is formed with a predominance of the 1-hydroxy-2-malonyl substituted product being present.

The above isomeric mixture (i.e., hexaethyl ester) is reacted with 250 milliliters of a 50% dioxane water mixture for a period of 24 hours at 80°C to form the complete phosphonate-malonate acid. This acid mixture is reacted with 1 liter of 8 N NaOH to form the hexa-sodium salt, i.e., $HC(COONa)_2CH_2C-(OH)(PO_3Na_2)_2$ and trace amounts of $H_2C(OH)C(PO_3Na_2)_2CH(COONa)_2$.

EXAMPLE XIV

Into a conventional reaction vessel are charged 51 grams of the tetraethyl ester of EEDP, 200 milliliters of propyl alcohol and 5 grams of sodium metal, which is dissolved in the propyl alcohol. The resulting mixture is heated to and maintained at 30°C, with continuous stirring, for 85 minutes. The resultant mass is cooled to 10°C and then 40 milliliters (abbreviated ml. herein) of a 20% by weight HCl aqueous solution is added to the aforementioned cooled mass, and the resultant material intimately stirred for a period of two minutes. The material is then filtered in a Buchner funnel; and the filtrate is collected and evaporated at 95°C to substantial dryness. The resultant solids are recrystallized in 100 ml. of water and dried again. $P^{31}$ and $H^1$ NMR and elemental analyses show the formation of two isomers which have the formulae $H_2C(C_3H_7O)C(OH)[PO_3(C_2H_5)_2]_2$ and $H_2C(OH)C(C_3H_7O)[PO_3-(C_2H_5)_2]_2$, with only trace amounts of the latter compound being present.

EXAMPLE XV

Into a reaction vessel such as that described in Example I are charged 104 grams of the acid form of EEDP and 250 milliliters of phenol. The resultant mass is then heated at about 100°C with reflux for a period of approximately eight hours. This reflux period is followed by vacuum (½ mm Hg) evaporation (80°C) to remove the excess phenol. The residue material is analyzed via $P^{31}$ and $H^1$ NMR and elemental analyses and show the formation of an isomeric mixture having formulae $H_2C(C_6H_5O)C(OH)(PO_3H_2)_2$ and $H_2C(OH)C(C_6H_5O)(PO_3H_2)_2$. The phenyl, ethyl and butyl esters of these isomers are prepared according to the procedure outlined in the last paragraph of Example II, utilizing, respectively, the esterification agent triphenyl orthoformate, triethyl orthoformate and tributyl orthoformate. The sodium, potassium and zinc salts of these isomers are prepared respectively by reacting stoichiometric quantities of the isomeric mixture (in acid form) with the respective metal hydroxide solution in order to form said salts.

EXAMPLE XVI

Into a reaction vessel such as that described in Example I are charged 104 grams of the acid form of EEDP and 250 milliliters of ethyl mercaptan which is at 20°C. The resultant mass is then heated at 55°C with reflux for a period of approximately six hours. This reflux period is followed by vacuum (5 mm Hg) evaporation (40°C) to remove the excess ethyl mercaptan. The residue material is analyzed via $P^{31}$ and $H^1$ NMR and elemental analyses and show the formation of an isomeric mixture having formulae $H_2C(SC_2H_5)C(OH)(PO_3H_2)_2$ and $H_2C(OH)C(SC_2H_5)(PO_3H_2)_2$.

EXAMPLE XVII

Example XVI is individually repeated three times, utilizing separately phenyl, methyl and butyl mercaptans in place of the ethyl mercaptan of Example XVI. The phenylthio, methyl thio and butyl thio derivatives of EEDP are formed in a similar fashion as the ethylthio derivative of Example XVI. The sodium, potassium and zinc salts of the resultant isomeric mixtures are prepared respectively by reacting stoichiometric quantities of the respective isomeric mixture with the respective metal hydroxide solution in order to form said salts.

EXAMPLE XVIII

Into a conventional reaction vessel equipped with a reflux condenser are charged 51 grams of the acid form of EEDP and 148 grams of isopropyl ether and 50 grams of zinc chloride. The resulting mass is heated under reflux for four hours at a temperature of approximately 70°C. The resultant product is filtered in order to remove the zinc chloride, and the filtrate is then subjected to evaporation at 90°C in order to remove the excess isopropyl ether. $P^{31}$ and $H^1$ NMR and elemental analyses show the formation of a compound having the formula $HC(O)CH(PO_3H_2)_2$. Example XVIII is twice separately repeated utilizing in place of zinc chloride and isopropyl ether (1) magnesium bromide and ethyl ether and (2) boron trifluoride and benzene. In each repeat, $P^{31}$ and $H^1$ NMR and elemental analyses show the formation of 2-oxy ethane-1,1-diphosphonic acid.

EXAMPLE XIX

In order to demonstrate one of the unique utilities of the compounds falling within Formula I heretofore described, the following example is carried out, illustrating the sequestering ability of the acid and salt forms of the novel ethane diphosphonates.

The testing procedure consists of pipetting an aliquot volume of 2.5% ferric chloride solution into a beaker and adding thereto enough sodium hydroxide or hydrochloric acid to give the desired pH. The solution is stirred for fifteen minutes, followed by the addition of an aliquot of 2.5% of the sequestering agent solution, i.e., the particular ethane diphosphonate (in the salt form) dissolved in water. After final pH adjustment with sodium hydroxide or hydrochloric acid, the solution is shaken for 48 hours to reach equilibrium. The solution is then centrifuged at 12,000 rpm for approximately 80 minutes to remove colloidal ferric hydroxide and an aliquot of the supernatant solution is titrated iodometrically or analyzed by X-ray fluorescence with use of an appropriate calibration curve in order to determine the ferric iron concentration. The ferric iron concentrations and sequestering agent concentrations found in parts per million (p.p.m.) are converted to a weight basis and expressed as pounds of iron sequestered by 100 pounds of sequestering agent.

Following the above described procedure, each of the compounds Nos. 1, 2, 5, 6, 8, 9, 10, 11, 13, 17, 18, 19, 21, 23, 24, 27, 28, 29, 30, 31, 33, 34, 35, 36, 40, 42, 43, 44 and 47 heretofore described and prepared according to the procedures outlined in this specification, including Examples I through XVIII, is individually tested. In each case it is found that the sequestering agents of the instant invention demonstrate an unexpected and unique ability to sequester ferric iron over a wide range of pH conditions, i.e., from about 4 to about 10.5, and that the average amount (in pounds) of iron sequestered by 100 pounds of the respective sequestering agent (compound No.) over the 4 to 10.5 pH range is 13, 15, 14, 5, 8, 7, 10, 11, 10, 12, 11, 9, 11, 7, 11, 6, 4, 7, 5, 6, 12, 12, 5, 11, 8, 6, 12, 8 and 7.

The above Example XIX is repeated several times with the exception that other metal ion-containing solutions such as calcium, copper, nickel and chromium are utilized in place of the ferric (chloride) solution. In each case utilizing the aforementioned compounds the average sequestration values of these latter mentioned ions respectively are found to be substantially similar to those set forth above.

Example XIX is again repeated several times, utilizing as a sequestering agent trisodium nitrilo triacetate ·2H₂O, sodium citrate, and potassium gluconate. It is found that the pounds of iron sequestered by 100 pounds of the aforementioned sequestering agents respectively are 7.0, 6.5 and 2.9 over the same pH range of 4 to 10.5. It can readily be seen, then, that the novel ethane diphosphonates (in the acid or salt forms) of the present invention when utilized as sequestering agents are equally as effective as the widely used organic sequestering agents under comparative conditions and in some cases are superior thereto. Furthermore, when said ethane diphosphonates of the present invention are utilized as sequestering agents, they exhibit an effectiveness as such over a wide range of pH conditions. This is highly advantageous in permitting their respective use in many and varied applications.

EXAMPLE XX

As illustrative of another demonstration of utility of the present invention ethane diphosphonates falling within Formula I, it is found that these materials also exhibit threshold properties, i.e., they can be utilized in less than stoichiometric quantities to prevent the precipitation of salts of mineral acids, such as $CaCO_3$, in aqueous systems. Specifically, a test is conducted in which each of the compounds set forth in Example XIX is separately and independently mixed at 25°C with 250 milliliters of water containing $CaCl_2$. To the resultant mixture is added $NaHCO_3$. The pH in each case is adjusted to 7 and maintained thereat with sufficient NaOH or HCl. The amounts of $CaCl_2$, $NaHCO_3$ and ethane diphosphonate used are sufficient to provide 5000 ppm of $CaCO_3$ and 10 ppm of ethane diphosphonate. It is observed in each case that these less than stoichiometric quantities of said threshold agents effect a substantially clear solution for a period of at least 48 hours. Stating the results in a different manner, 10 parts per million of the ethane diphosphonate threshold agent is effective in providing a clear solution without precipitation which contains substantially greater than stoichiometric quantities of calcium carbonate therein.

EXAMPLE XXI

In order to demonstrate the utility of the esters of the ethane diphosphone compounds falling within Formula I, approximately 50 grams of each of compounds Nos. 3, 4, 7, 12, 14, 16, 20, 22, 25, 26, 32, 37, 38, 39, 41, 45, 46 and 48, heretofore described and prepared according to the procedures outlined in this specification, including Examples I through XVIII, are separately and individually mixed with an inert solvent in a 500 milliliter beaker, in this case carbon tetrachloride, in order to prepare a 10% by weight (solution or) slurry of each ester. After the separate slurries are prepared, a separate and individual swatch of a 3 inches × 3 inches undyed cotton cellulose is intimately contacted with each slurry by submerging such swatch in the slurry for approximately five minutes. The separate swatches are withdrawn from the beakers containing these slurries (or solutions) and are dried for fifteen minutes in an oven which is maintained at a temperature of approximately 80°C. After a lapse of fifteen minutes at 80°C, the temperature is elevated and the swatches are then subjected to a temperature of approximately 150°C for ten minutes in order to "set up" a reaction between the specific esters with the surface groups on the cotton cellulose.

The individual, dried swatches of "treated" cotton are individually tested for flame retardancy by positioning a swatch over a bunsen burner. The flame is adjusted to a point at which the tip of the flame is approximately one inch beneath the cotton swatch and untreated cotton swatch is used as a control for comparative purposes. The flame underneath each of the individual cotton swatches (including the control) is maintained for approximately 35 seconds, and then is removed. Visual observations are made. The results of this test show that the control sample, i.e., the cotton swatch which was not treated with any esters heretofore mentioned, is completely destroyed. However, with each of the individually treated cotton swatches, there is primarily only charring, and the flame on the material is extinguished within about 5 seconds upon the removal of the bunsen burner away from the cotton swatches. Thus, it can readily be seen that one of the unique applications of the esters of the ethane diphosphonates falling within Formula I is their use as a fire retardant for cellulose material, for example, cotton clothing.

What is claimed is:

1. An ethane diphosphonate of the formula

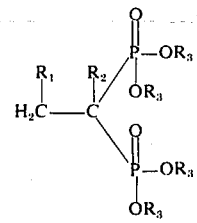

wherein each $R_3$ is individually selected from the group consisting of hydrogen, alkali metal ions, alkaline earth metal ions, ammonium ions and lower alkyl amine ions and $R_1$ and $R_2$ are either hydroxy or a $-OR_5$ or $-SR_5$ group where $R_5$ is $C_{1-8}$ alkyl, phenyl, or benzyl, provided that $R_1$ or $R_2$ but not both is always hydroxy.

2. 2-thiomethyl-1-hydroxyethane-1,1-diphosphonic acid.

3. A compound of claim 1 wherein $R_2$ is hydroxy.

4. A compound of claim 1 which is 2-methoxy-1-hydroxy ethane-1,1-diphosphonic acid.

5. A compound of claim 1 which is 2-hydroxy-1-methoxy ethane-1,1-diphosphonic acid.

6. A compound of claim 1 which is disodium 2-ethoxy-1-hydroxy ethane-1,1-diphosphonate.

7. A compound of claim 1 which is 2-phenoxy-1-hydroxy ethane-1,1-diphosphonic acid.

8. A compound of claim 1 which is 2-thiophenyl, 1-hydroxy ethane-1,1-diphosphonic acid.

* * * * *